(12) United States Patent
Hart et al.

(10) Patent No.: US 9,588,081 B2
(45) Date of Patent: *Mar. 7, 2017

(54) INTERDIGITATED ELECTRODE CONFIGURATION FOR ION FILTER

(71) Applicant: Owlstone Limited, Cambridge (GB)

(72) Inventors: Matthew Hart, London (GB); Andrew H. Koehl, Cambridge (GB)

(73) Assignee: Ownstone Medical Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,994

(22) Filed: Oct. 8, 2015

(65) Prior Publication Data

US 2016/0025679 A1    Jan. 28, 2016

Related U.S. Application Data

(63) Continuation-in-part of application No. 12/442,921, filed as application No. PCT/GB2007/050581 on Sep. 25, 2007, now Pat. No. 9,177,769.

(51) Int. Cl.
*H01J 49/00* (2006.01)
*G01N 27/62* (2006.01)
*H01J 49/42* (2006.01)

(52) U.S. Cl.
CPC .......... *G01N 27/622* (2013.01); *H01J 49/421* (2013.01); *G01N 27/624* (2013.01)

(58) Field of Classification Search
CPC .... H01J 49/00; H01J 49/0013; H01J 49/0018; H01J 49/02; H01J 49/025; H01J 49/06; H01J 49/061; H01J 49/062; H01J 49/063; H01J 49/065; H01J 49/067; H01J 49/068; H01J 49/26; H01J 49/28; H01J 49/282
USPC ........ 250/281, 282, 287, 290, 291, 293, 294
See application file for complete search history.

(56) References Cited

U.S. PATENT DOCUMENTS

| 5,465,480 A * | 11/1995 | Karl ..................... G01N 27/622 29/602.1 |
| 9,177,769 B2 * | 11/2015 | Hart ..................... G01N 27/622 |
| 2007/0040113 A1 * | 2/2007 | Monroe ............... G06N 99/002 250/290 |

\* cited by examiner

*Primary Examiner* — Jason McCormack
(74) *Attorney, Agent, or Firm* — Locke Lord LLP; Barry Kramer; Christopher J. Capelli

(57) ABSTRACT

An ion filter and a method of manufacturing an ion filter. The method including providing a monolithic structure; selectively removing regions of the structure, to form a pair of electrodes defining at least one ion channel therebetween. The electrodes are preferably mechanically connected at one or more locations by a portion of the structure; wherein the connecting portion of the structure provides a higher electrical impedance than the filter would provide without such a mechanical connection, to thereby electrically separate the electrodes.

40 Claims, 2 Drawing Sheets

22

INTERDIGITATED ELECTRODE CONFIGURATION FOR ION FILTER

CROSS REFERENCE TO RELATED APPLICATIONS

This application claims priority to, and in a continuation-in-part of U.S. patent application Ser. No. 12/442,921 filed Jan. 29, 2010 which is incorporated herein by reference in its entirety, which claims priority to PCT Patent Application No. PCT/GB2007/050581, filed Sep. 25, 2007.

FIELD OF THE INVENTION

The present invention relates to an ion filter comprising a particular electrode structure, and to a method of manufacturing such an ion filter. The filter is particularly suitable for use in ion mobility spectrometry, and in an ion pump.

BACKGROUND TO THE INVENTION

Ion mobility spectrometry is a versatile technique used to detect presence of molecular species in a gas sample. The technique has particular application in detection of explosives, drugs, and chemical agents in a sample, although it is not limited to these applications. Portable detectors are commonly used for security screening, and in the defense industry.

Ion mobility spectrometry relies on the differential movement of different ion species through an electric field to a detector; by appropriate selection of the parameters of the electric field, ions having differing properties will reach the detector at differing times, if at all. Time of flight (TOF) ion mobility spectrometry measures the time taken by ions when subject to an electric field to travel along a drift tube to a detector against a drift gas flow. By varying the electric field ions of different characteristics will reach the detector at different times, and the composition of a sample can be analysed. This form of spectrometry relies on the length of the drift tube for its resolution; the longer the drift tube, the more powerful the detector.

A variation on TOF ion mobility spectrometry is described in U.S. Pat. No. 5,789,745, which makes use of a moving electrical potential to move ions against a drift gas flow towards a detector. A plurality of spaced electrodes are alternately pulsed to generate a moving potential well, which carries selected ions along with it.

Field asymmetric ion mobility spectrometry (FAIMS) is a derivative of time of flight ion mobility spectrometry (TOFIMS), which potentially offers a smaller form factor; however, existing designs use moving gas flows and high voltages, which are undesirable for microchip implementations. Scaling is further hindered by molecular diffusion, an effect that becomes significant in the micron regime. Background information relating to FAIMs can be found in L. A. Buryakov et al. Int. J. Mass. Spectrom. Ion Process. 128 (1993) 143; and E. V. Krylov et al. Int. J. Mass. Spectrom. Ion Process. 225 (2003) 39-51; hereby incorporated by reference.

A further modification of FAIMS is described in international patent publications WO2006/013396 and WO2006/046077, the contents of which are incorporated herein by reference. The devices described in these publications make use of an electric field to cause ions to move toward the detector, and an ion filter comprising paired interdigitated electrode structures defining a plurality of ion channels through which ions may selectively pass, depending on the electric field applied between the electrodes. The paired electrodes must be electrically separated from one another; this is achieved by mechanical separation of the electrodes by forming them on an insulating substrate. To manufacture these electrodes, they must either be separately manufactured and then bonded onto a substrate, or they must be formed directly on the substrate.

As described in WO2006/013396, the electrodes may be manufactured using largely conventional microfabrication techniques. A conductive material is deposited on the top and bottom faces of a high resistivity silicon wafer substrate, followed by a photo resistant coating on each face. The top face is masked and subjected to photolithography, after which the coating of the top face is wet etched to provide an array of electrodes. The photoresist is stripped from both faces, and the process repeated to form the bottom face electrodes. A further resist coating is applied to the top face, after which the silicon is etched from the lower face using deep reactive ion etching to form channels. The photoresist is stripped for the final time, and the filter is ready for further processing.

In a variation of this technique, the silicon wafer may be initially bonded on the bottom face to a glass substrate; the various etching steps are then carried out from the top face to create channels and electrodes, after which the glass substrate is acid etched to expose the bottom face of the wafer, leaving a glass support in contact with the wafer.

The ion filter structure so produced may then be used in an ion mobility spectrometer device; or may be used in an ion pump, as described in GB 0521451.5.

A monolithic quadrupole mass spectrometer is described in GB 2 391 694, while US 2001/0042826 describes an ion filter including a two-dimensional array of poles forming one or more quadrupoles.

It would be advantageous to provide an alternative means of manufacturing an ion filter. In particular, it would be advantageous to reduce or remove the need for an insulative substrate.

SUMMARY OF THE INVENTION

According to a first aspect of the present invention, there is provided a method of manufacturing an ion filter, the method comprising providing a monolithic structure; selectively removing regions of the structure, to form a pair of electrodes defining at least one ion channel therebetween; the electrodes further being mechanically connected at one or more locations by a portion of the structure; wherein the connecting portion of the structure provides a higher electrical impedance than the filter would provide without such a mechanical connection, to thereby electrically separate the electrodes.

Preferably the monolithic structure comprises a wafer material, for example a silicon wafer. By 'monolithic', we mean that the structure is a single material, and is not made from a composite of separate materials.

This manufacturing process allows the paired electrodes of the ion filter to be produced from a single wafer, without the need to either deposit conductive regions on a substrate, or to form the electrodes separately and then secure them to a substrate. In addition, where the prior art makes use of a substrate, this substrate must also be etched to form suitable ion channels; this additional etching step is not necessary for the present invention.

Preferably the higher impedance of the connecting portion is obtained over the frequency range at which the filter is intended to operate; such higher impedances may also be obtained outside this range, but this is not essential.

Preferably the electrodes are interdigitated electrodes, each having at least one elongate finger.

The method may further comprise treating the connecting portion to alter its electrical impedance; preferably the treatment increases electrical impedance. Alternatively, or in addition, the method may comprise treating the electrodes to alter their electrical impedance; preferably the impedance is decreased. The precise treatment to be used will depend on the nature of the materials from which the filter is made, the desired alteration, and the desired level of impedance after treatment. For example, the structure may be doped, for example with boron, antimony, arsenic, or phosphorous. Suitable materials for the structure include silicon, which is most preferred, as well as germanium or gallium arsenide. The skilled person will be aware of other suitable materials for the structure and suitable dopants. Alternatively, the structure may be put under stress to alter its electrical impedance. A further approach is to locally chemically or otherwise modify the structure; for example, a silicon wafer may be oxidised to form silicon oxide which will alter the impedance of that portion of the wafer. Silicon nitride may also be used.

The connecting portion or the electrodes may be treated to alter impedance either before or after selective removal of regions of the structure. Preferably treatment takes place before selective removal of regions of the structure.

As an alternative to treating the electrodes or connecting portion to alter impedance, or in addition to such treatment, the method may comprise selecting one or more predetermined physical dimensions of the connecting portion and/or the electrodes to obtain a desired electrical impedance. In particular, the cross-sectional area of the connecting portion and/or the electrodes may be so selected; or the length to cross-sectional area ratio may be so selected. Other physical dimensions are suitable for such selection; the skilled person will be aware of how these may be selected to give a desired impedance.

Preferably the electrodes define one or more elongate fingers and an edge region, and the connecting portion is located in the edge region. Alternatively, or in addition, the connecting portion may be located on the elongate fingers; this may be at the tip or along the length of the fingers, provided there is sufficient unconnected space to define suitable ion channels.

A plurality of connecting portions may be present.

Preferably the electrodes each comprise a plurality of elongate fingers, defining between them a plurality of ion channels. The fingers may in certain embodiments be curved or serpentine, thereby defining similarly curved or serpentine ion channels.

Preferably a plurality of ion channels are present; preferably at least 5, at least 10, at least 15, or at least 20 ion channels.

The method may further comprise bonding the monolithic structure to a substrate.

According to a further aspect of the present invention, there is provided an ion filter comprising a monolithic structure defining a pair of electrodes defining at least one ion channel therebetween; the electrodes further being mechanically connected at one or more locations by a portion of the monolithic structure; wherein the connecting portion provides a higher electrical impedance than the filter would provide without such a mechanical connection, to thereby electrically separate the electrodes.

The monolithic structure is preferably a wafer, for example a silicon wafer.

The connecting portion may be treated, for example it may be doped or chemically altered, to alter its electrical impedance. Alternatively, or in addition, the electrodes may be so treated.

Alternatively, or in addition, the connecting portion and/or the electrodes may have one or more predetermined physical dimensions selected to obtain a desired electrical impedance. In particular, the cross-sectional area of the connecting portion and/or the electrodes may be so selected; or the length to cross-sectional area ratio may be so selected. Other physical dimensions are suitable for such selection; the skilled person will be aware of how these may be selected to give a desired impedance.

Preferably the electrodes define one or more elongate fingers and an edge region, and the connecting portion is located in the edge region. Alternatively, or in addition, the connecting portion may be located on the elongate fingers; this may be at the tip or along the length of the fingers, provided there is sufficient unconnected space to define suitable ion channels.

A plurality of connecting portions may be present.

Preferably the electrodes each comprise a plurality of elongate fingers, defining between them a plurality of ion channels. The fingers may in certain embodiments be curved or serpentine, thereby defining similarly curved or serpentine ion channels.

Preferably a plurality of ion channels are present; preferably at least 5, at least 10, at least 15, or at least 20 ion channels.

The ion filter may further comprise a substrate on which the structure is bonded.

A further aspect of the present invention provides an ion mobility spectrometer comprising an ioniser, an ion filter as herein described, and an ion detector. The spectrometer may further comprise means for driving ions through the ion filter; for example, a gas flow generator, and/or paired electrodes for generating a drive electric field through the filter. Other features of the spectrometer may be as described in WO2006/013396 and WO2006/046077, the contents of which are incorporated herein by reference.

A still further aspect of the present invention provides an ion pump incorporating an ion filter as herein described. There is provided a device for selectively transferring ionised species from a first space to a second space, the device comprising first and second spaces separated by an ion filter allowing selective communication between the spaces; the ion filter being as herein described. Other features of the device may be as disclosed in GB 0521451.5.

BRIEF DESCRIPTION OF THE DRAWINGS

These and other aspects of the present invention will now be described by way of example with reference to the accompanying drawings, in which.

DETAILED DESCRIPTION OF THE DRAWINGS

Figure 1:
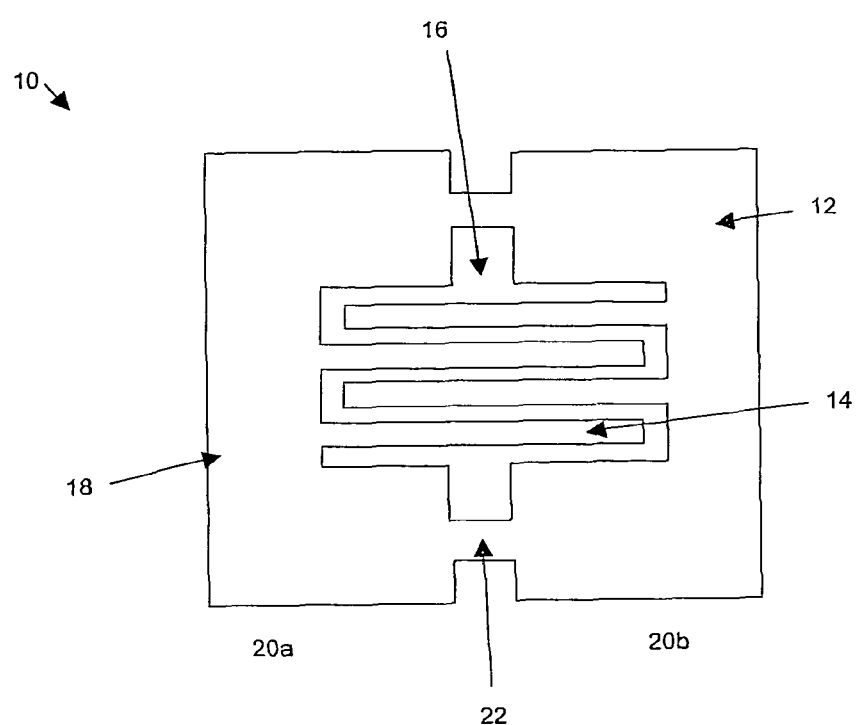
FIG. 1 shows a first embodiment of an ion filter according to an aspect of the present invention.

Referring to the Figures, these show first and second embodiments of an ion filter according to the present invention. The filter 10 is formed of a doped silicon wafer 12 which is initially solid. The wafer is typically around 0.3 mm in thickness. The wafer 12 is etched by means of deep reactive ion etching or other chemical or physical etching techniques in order to form a number of elongate fingers 14. The fingers between them define a number of ion channels 16 extending through the depth of the wafer. An outer edge 18 is left surrounding the fingers and channels. The elongate electrode fingers 14 and part of the edge 18 together define two distinct portions of the filter 10. The two portions 20 *a*, 20 *b* are connected mechanically by bridges 22 between the two portions formed in the edge 18.

The bridges 22 are formed so as to have a greater electrical impedance than the remainder of the ion filter, and in particular the electrode fingers 14. In a first embodiment, shown in FIG. 1, the dimensions of the bridges are chosen to provide a suitable impedance. For example, two bridges each with dimensions 1 mm long, 1 mm wide and 0.3 mm thick, made from a material with resistivity 2000 Ohm cm would have a combined parallel resistance just over 30 k Ohms.

Figure 2:
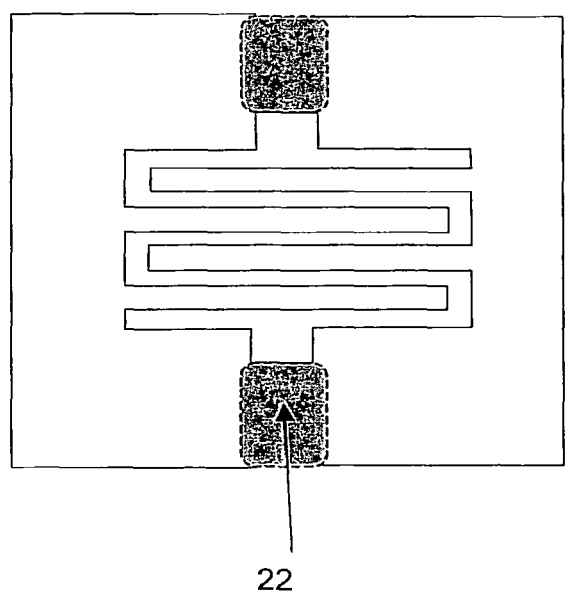
FIG. 2 shows a second embodiment of an ion filter according to an aspect of the present invention.

Alternatively, the wafer material may be doped or otherwise modified, for example by oxidation, at the bridges 22; this is illustrated in FIG. 2.

In yet another embodiment provided is an ion filter that comprises a monolithic structure defined by at least one ion channel forming at least two separated interdigitated electrodes and at least one connecting portion that holds the at least two interdigitated electrodes in fixed positions relative to one another. It is to be appreciated an embodiment may include a plurality of ion channels. The monolithic structure may be bonded to at least one support structure that includes at least one electrically insulating layer and wherein the at least one support structure provides at least one mechanical linkage that holds the at least two interdigitated electrodes in fixed positions relative to one another and wherein part of the monolithic structure is absent (e.g., such as the at least one connecting portion).

The at least one connecting portion is structured to allow an electrical impedance in a target range to be established between the at least two electrodes to thereby partially or fully electrically separate the electrodes. It is noted the electrodes may define one or more elongate fingers and the at least one connecting portion is formed or located on the elongate fingers and may define one or more elongate fingers and an edge region, and the at least one connecting portion is formed or located on the edge region. It is to be appreciated the electrodes may each have a plurality of elongate fingers, defining between them a plurality of ion channels wherein the fingers may be curved or serpentine.

The at least one connecting portion and/or the electrodes may be treated to change their electrical impedance and/or have one or more predetermined physical dimensions selected to obtain a desired electrical impedance. Further, the connecting portion may be held at a defined electrical potential with respect to the electrodes to maintain a prescribed electrical impedance between the electrodes. The at least one connecting portion may have a high electrical impedance so as to be used as an electrical insulator.

In another embodiment, a method of manufacturing an ion filter may include providing a monolithic structure and selectively adding and/or removing one or more regions of the structure to form at least one ion channel so as to form at least two separated interdigitated electrodes and at least one connecting portion that holds the at least two interdigitated electrodes in fixed positions relative to one another. It is noted the electrodes may define one or more elongate fingers and the at least one connecting portion is formed or located on the elongate fingers. The electrodes may also define one or more elongate fingers and an edge region, and the at least one connecting portion is formed or located on the edge region.

The monolithic structure may be bonded to at least one support structure that includes at least one electrically insulating layer wherein the at least one support structure provides at least one mechanical linkage that holds the at least two interdigitated electrodes in fixed positions relative to one another. Additionally, an electrical impedance is provided that is in a target range produced by removal of part of the monolithic structure after mounting to the at least one support structure.

The at least one connecting portion is structured to allow an electrical impedance in a target range to be established between the at least two electrodes, to thereby partially or fully electrically separate the electrodes. It is to be appreciated the at least one connecting portion and/or the electrodes may be treated to alter electrical impedance, for example to increase or decrease electrical impedance. The treatment may include doping or locally chemically modifying the monolithic structure to alter impedance. Further, the treatment may occur before, during, between, or after the selective removal of one or more regions of the structure. Additionally, one or more predetermined physical dimensions of the at least one connecting portion and/or the electrodes may be selected to obtain a desired electrical impedance.

Additionally, material may be selectively added to the structure wherein the added material forms the at least one connecting portion that holds the at least two interdigitated electrodes in fixed positions relative to one another and wherein the added material has a high electrical impedance, for example being an electrical insulator.

In yet still another embodiment, provided is an ion mobility spectrometer comprising an ionizer, an ion filter as described above, and an ion detector. In another embodiment, provided is a device for selectively transferring ionized species from a first space to a second space, wherein the device preferably includes first and second spaces separated by an ion filter (as described above) allowing selective communication between the spaces.

Thus, the present invention incorporates a mechanical linkage between the two electrodes into the same wafer used to form the electrodes themselves, rather than using a separate substrate. This mechanical linkage must still provide electrical isolation between the two electrodes; this can be done by forming the device from a suitable material (e.g. doped silicon) and ensuring that the regions forming the mechanical linkages have a high enough ratio of length to effective cross-sectional area to achieve the required isolation resistance for the resistivity used, or by selectively doping or otherwise modifying the material to form mechanical linkages that also achieve electrical isolation. In certain embodiments, both of these methods may be used.

What is claimed is:

1. A method of manufacturing an ion filter, the method comprising,
   providing a monolithic structure;
   selectively removing one or more regions of the structure to form at least one ion channel so as to form at least two separated interdigitated electrodes and at least one connecting portion that holds the at least two interdigitated electrodes in fixed positions relative to one another, wherein the at least one connecting portion is structured to allow an electrical impedance in a target range to be established between the at least two electrodes, to thereby partially or fully electrically separate the electrodes.

2. The method of claim 1 further comprising treating the at least one connecting portion and/or the electrodes to alter electrical impedance.

3. The method of claim 2 wherein the treatment comprises doping.

4. The method of claim 2 wherein the treatment comprises locally chemically modifying the monolithic structure to alter impedance.

5. The method of claim 2 wherein treatment takes place before, during, between, or after the selective removal of one or more regions of the structure.

6. The method of claim 1 comprising selecting one or more predetermined physical dimensions of the at least one connecting portion and/or the electrodes to obtain a desired electrical impedance.

7. The method of claim 1 wherein the electrodes define one or more elongate fingers and the at least one connecting portion is formed or located on the elongate fingers.

8. The method of claim 1 wherein the electrodes define one or more elongate fingers and an edge region, and the at least one connecting portion is formed or located on the edge region.

9. The method of claim 1 further comprising bonding the monolithic structure to at least one support structure that includes at least one electrically insulating layer.

10. The method of claim 9 wherein the at least one support structure provides at least one mechanical linkage that holds the at least two interdigitated electrodes in fixed positions relative to one another.

11. The method of claim 10 wherein the electrical impedance in the target range is produced by removal of a portion of the monolithic structure after mounting to the at least one support structure.

12. The method of claim 1 further comprising selectively adding material to the structure.

13. The method of claim 1 wherein the added material forms the at least one connecting portion that holds the at least two interdigitated electrodes in fixed positions relative to one another.

14. The method of claim 13 wherein the added material has a high electrical impedance.

15. A method of manufacturing an ion filter, the method comprising:
providing a monolithic structure and/or substrate;
selectively adding and/or removing one or more regions of the structure and/or substrate to form at least one ion channel so as to form at least two interdigitated electrodes and at least one connecting portion that holds the at least two interdigitated electrodes in fixed positions relative to one another, wherein the at least one connecting portion is structured to allow an electrical impedance in a target range to be established between the at least two electrodes to thereby partially or fully electrically separate the electrodes.

16. The method of claim 15 further comprising treating the at least one connecting portion and/or the electrodes to alter the electrical impedance.

17. The method of claim 16 wherein the treatment comprises doping.

18. The method of claim 16 wherein the treatment comprises locally chemically modifying the monolithic structure to alter impedance.

19. The method of claim 16 wherein treatment takes place before, during, between, or after the selective addition and/or removal of one or more regions of the structure.

20. The method of claim 15 comprising selecting one or more predetermined physical dimensions of the at least one connecting portion and/or the electrodes to obtain a desired electrical impedance.

21. The method of claim 15 wherein the electrodes define one or more elongate fingers and the at least one connecting portion is formed or located on the elongate fingers.

22. The method of claim 15 wherein the electrodes define one or more elongate fingers and an edge region, and the at least one connecting portion is formed or located on the edge region.

23. The method of claim 15 further comprising bonding the monolithic structure to at least one support structure that includes at least one electrically insulating layer.

24. The method of claim 15 wherein the at least one support structure provides at least one mechanical linkage that holds the at least two interdigitated electrodes in fixed positions relative to one another.

25. The method of claim 24 wherein the electrical impedance in the target range is produced by removal of a portion of the monolithic structure after mounting to the at least one support structure.

26. An ion filter comprising a monolithic structure defining at least one ion channel forming at least two separated interdigitated electrodes and at least one connecting portion that holds the at least two interdigitated electrodes in fixed positions relative to one another wherein the at least one connecting portion is structured to allow an electrical impedance in a target range to be established between the at least two electrodes, to thereby partially or fully electrically separate the electrodes.

27. The filter of claim 26 wherein the at least one connecting portion and/or the electrodes are treated to change their electrical impedance.

28. The filter of claim 26 wherein the at least one connecting portion and/or the electrodes have one or more predetermined physical dimensions selected to obtain a desired electrical impedance.

29. The filter of claim 26 wherein the connecting portion is held at a defined electrical potential with respect to the electrodes to maintain a prescribed electrical impedance between the electrodes.

30. The filter of claim 26 wherein the electrodes define one or more elongate fingers and the at least one connecting portion is formed or located on the elongate fingers.

31. The filter of claim 26 wherein the electrodes define one or more elongate fingers and an edge region, and the at least one connecting portion is formed or located on the edge region.

32. The filter of claim 26 further comprising a monolithic structure that is bonded to at least one support structure that includes at least one electrically insulating layer.

33. The filter of claim 32 wherein the at least one support structure provides at least one mechanical linkage that holds the at least two interdigitated electrodes in fixed positions relative to one another.

34. The filter of claim 33 wherein part of the monolithic structure is absent.

35. The filter of claim 26 wherein the at least one connecting portion has a high electrical impedance so as to be used as an electrical insulator.

36. The filter of claim 26 wherein the electrodes each comprise a plurality of elongate fingers, defining between them a plurality of ion channels.

37. The filter of claim 36 wherein the fingers are curved or serpentine.

38. The filter of claim 26 wherein a plurality of ion channels are present.

39. An ion mobility spectrometer comprising an ioniser, an ion filter as described in claim 26, and an ion detector.

40. A device for selectively transferring ionised species from a first space to a second space, the device comprising first and second spaces separated by an ion filter allowing selective communication between the spaces; the ion filter being as described in claim 26.

* * * * *